United States Patent [19]
Fischell et al.

[11] Patent Number: 5,643,312
[45] Date of Patent: Jul. 1, 1997

[54] STENT HAVING A MULTIPLICITY OF CLOSED CIRCULAR STRUCTURES

[76] Inventors: Robert E. Fischell, 14600 Viburnum Dr., Dayton, Md. 21036; David R. Fischell, 71 Riverlawn Dr., Fair Haven, N.J. 07704; Tim A. Fischell, 1018 Chancery La., Nashville, Tenn. 37215

[21] Appl. No.: 202,128

[22] Filed: Feb. 25, 1994

[51] Int. Cl.$^6$ .................................................. A61M 29/00
[52] U.S. Cl. ........................... 606/198; 623/1; 623/12
[58] Field of Search ............................ 606/108, 191, 606/194, 195, 198, 200; 623/1, 12

[56] References Cited

U.S. PATENT DOCUMENTS

| | | |
|---|---|---|
| 4,503,569 | 3/1985 | Dotter . |
| 4,553,545 | 11/1985 | Mass et al. . |
| 4,580,568 | 4/1986 | Gianturco . |
| 4,681,110 | 7/1987 | Wilztor . |
| 4,733,665 | 3/1988 | Palmaz . |
| 4,739,762 | 4/1988 | Palmaz . |
| 4,795,458 | 1/1989 | Regan . |
| 5,192,307 | 3/1993 | Wall . |
| 5,266,073 | 11/1993 | Wall . |
| 5,269,802 | 12/1993 | Garber ........................ 623/12 |
| 5,290,305 | 3/1994 | Inoue ........................... 623/12 |
| 5,443,500 | 8/1995 | Sigwart . |
| 5,496,365 | 3/1996 | Sgro ............................. 623/1 |

FOREIGN PATENT DOCUMENTS

| | | |
|---|---|---|
| 566807 | 10/1993 | European Pat. Off. . |
| 662307 | 7/1995 | European Pat. Off. . |

*Primary Examiner*—Michael Buiz
*Assistant Examiner*—William W. Lewis
*Attorney, Agent, or Firm*—Morton J. Rosenberg; David I. Klein

[57] ABSTRACT

The present invention provides for an expandable stent (1) for use in an artery or other vessel of a human body which forms a plurality of spaced apart generally circular rings (2). The stent structure (1) maintains patency of a vessel within which the stent (1) is inserted and is formed by a plurality of closed and generally circular rings (2) where the plane of each ring (2) is substantially parallel to the plane of an adjacent ring (2). The rings (2) have a common longitudinal axis generally perpendicular to the plane of each ring (2) with the longitudinal axis passing through the geometric center of each of the rings (2). A plurality of elongated wire structures forming longitudinals (4T, 4B, 4R, 4L) are fixedly secured to the rings (2) and extend in a direction generally parallel to the longitudinal axis of the rings (2). The stent (1) formed of the generally circular rings (2) optimizes hoop strength and minimizes elastic recoil of a vessel into which the stent (1) is inserted.

23 Claims, 4 Drawing Sheets

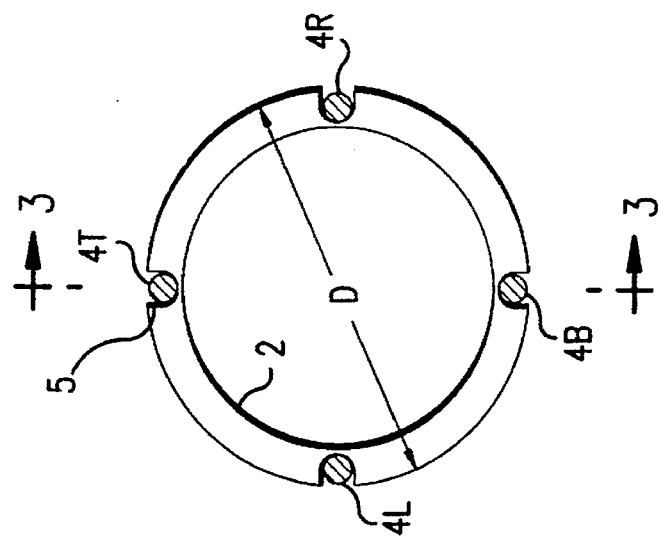
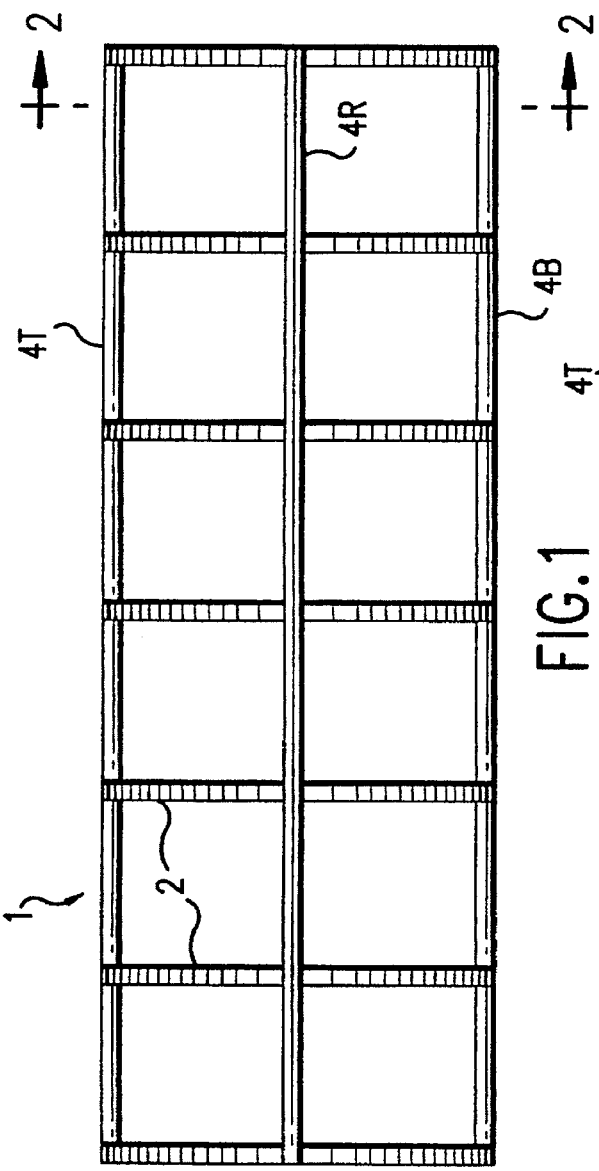
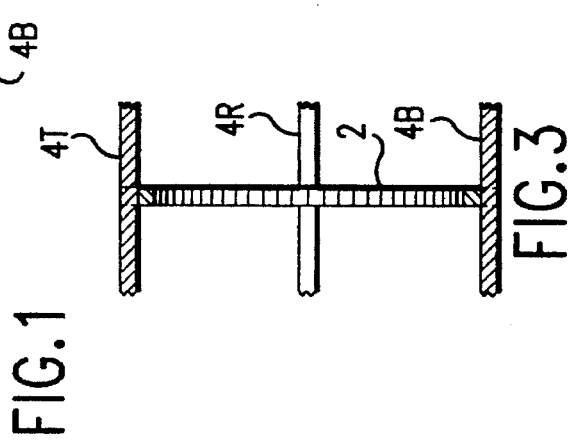

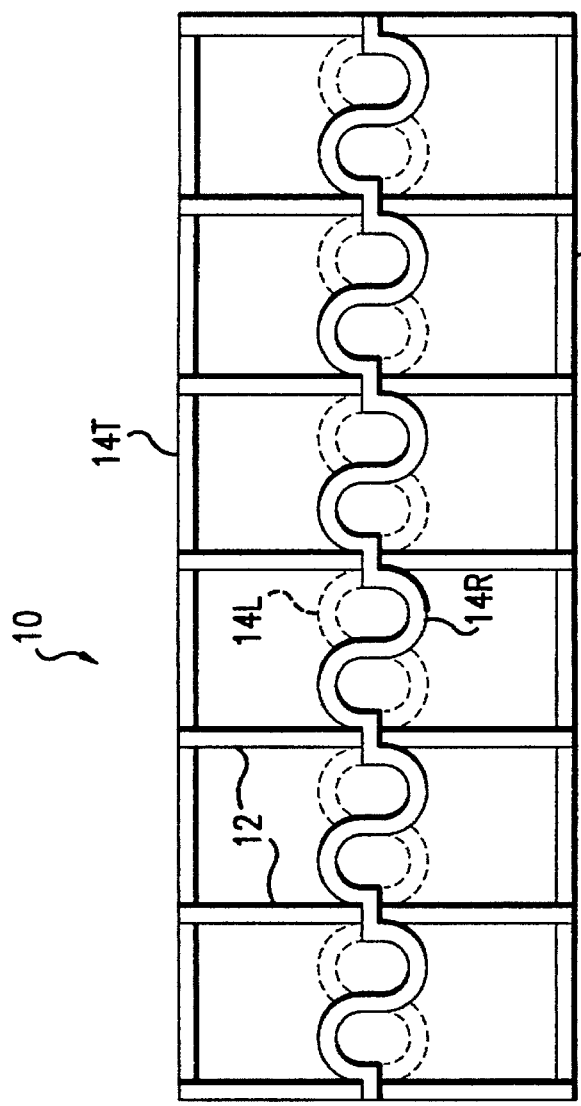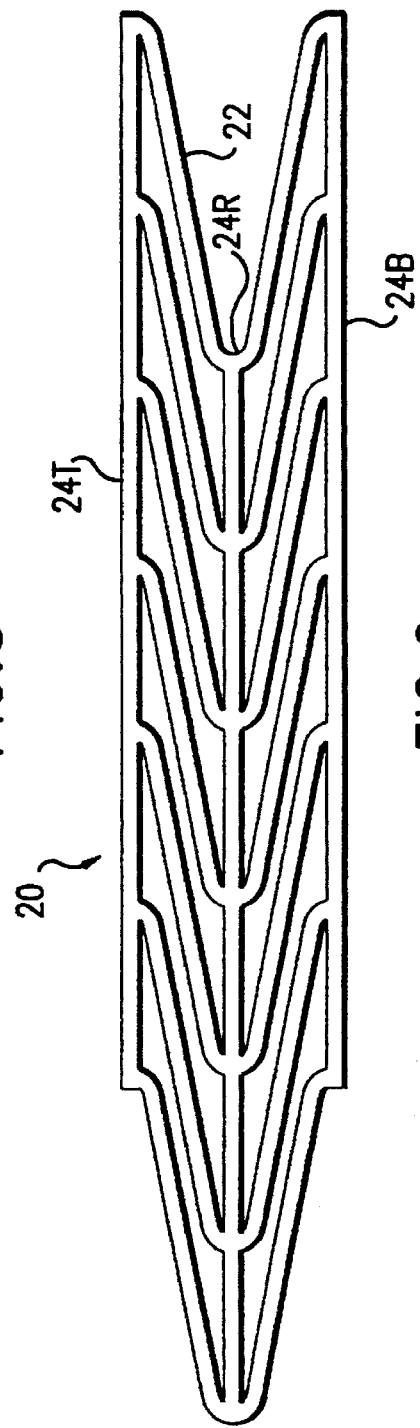

STENT HAVING A MULTIPLICITY OF CLOSED CIRCULAR STRUCTURES

FIELD OF THE INVENTION

This invention is in the field of stents for maintaining patency of any one of a multiplicity of vessels of the human body.

BACKGROUND OF THE INVENTION

In the last decade, many different designs of stents have been used to maintain patency of arteries and other vessels of the human body. In all such devices, hoop strength is an important characteristic. Specifically, the stent must have enough hoop strength to resist the elastic recoil exerted by the vessel into which the stent is placed. The Mass stent described in the U.S. Pat. No. 4,553,545 and the Dotter stent described in U.S. Pat. No. 4,503,569 are each open helical coils. The Palmaz stent described in the U.S. Pat. No. 4,733,665 is of the "chinese finger" design. The Gianturco-Rubin stent currently sold by Cook, Inc. is another stent design which like the stents of Mass, Dotter and Palmaz does not have any closed circular member to optimize hoop strength.

The ideal arterial stent utilizes a minimum wire size of the stent elements to minimize thrombosis at the stent site after implantation. The ideal arterial stent also possesses sufficient hoop strength to resist elastic recoil of the artery. Although the optimum design for maximizing hoop strength is a closed circular structure, no prior art stent has been described which has a small diameter when percutaneously inserted into a vessel and which expands into the form of multiplicity of closed circular structures (i.e. rings) when expanded outward against the vessel wall.

BRIEF SUMMARY OF THE PRESENT INVENTION

The present invention is an expandable stent that can be used in an artery or any other vessel of the human body which, when expanded, forms a mutiplicity of generally circular rings whose closed structure optimizes hoop strength so as to minimize elastic recoil of the vessel into which the stent is inserted. Furthermore, the structure of the stent in the present invention is initially in the form of folded ellipses or ovals which can be formed to a small diameter for percutaneous insertion by means of a stent delivery catheter. The ovals are joined to each other by either a straight or undulating shaped wires which are called "longitudinals" which serve to space the deployed rings within the vessel. Straight longitudinals are used in straight vessels and undulating longitudinals can be employed in either straight or highly curved vessels such as some coronary arteries.

Thus, an object of this invention is to provide a stent having a maximum hoop strength by the employment of closed, generally circular structures which are in fact rings.

Another object of this invention is that the rings are initially in the form of ovals that can be folded to fit onto a cylindrical structure at a distal portion of a stent delivery catheter.

Still another object of this invention is that the fully deployed rings are spaced apart by means of longitudinals which are either straight of undulating wires that are placed to be generally parallel to the longitudinal axis of the vessel into which the stent is deployed.

Still another object of this invention is that the pre-deployment stent structure is formed as a single piece out of a metal tube having a smaller inside diameter as compared to the outside diameter of an expandable balloon onto which the pre-deployment stent is mounted.

These and other important objects and advantages of this invention will become apparent from the detailed description of the invention and the associated drawings provided herein.

BRIEF DESCRIPTION OF THE DRAWINGS

FIG. 1 is a side view of the stent after it has been deployed; i.e., in its post-deployment form.

FIG. 2 is a transverse cross section at section 2—2 of FIG. 1 illustrating how the longitudinals are joined to the rings.

FIG. 3 is a cross section at section 3—3 of FIG. 2 showing the joining of a single ring to the longitudinals.

FIG. 8 is a side view of a post-deployment stent structure which utilizes two undulating longitudinals on opposite sides of the stent for improved placement in curved vessels.

FIG. 9 is a side view of a stent as etched out of a small diameter metal cylinder as a single piece of metal.

DETAILED DESCRIPTION OF THE DRAWINGS

Figure 5:
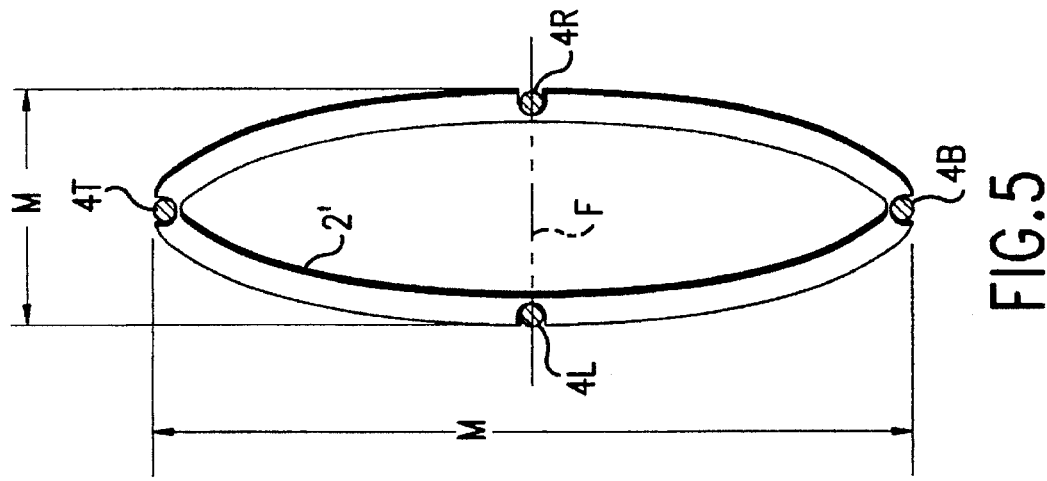
FIG. 5 is a transverse cross section at section 5—5 of FIG. 4 illustrating how the longitudinals are joined to the ovals.

FIG. 1 is a side view of the cylindrical stent 1 of the present invention shown in its post-deployment configuration. The stent 1 has a multiplicity of rings 2 which are spaced apart by four wires called longitudinals. As seen in FIGS. 1 and 2, at the top of the stent is longitudinal 4T, at the bottom is longitudinal 4B, at the left side is longitudinal 4L and at the right side is longitudinal 4R. Although FIGS. 1 and 2 show 7 rings and 4 longitudinals, it is apparent that the stent can be made longer by adding rings or increasing the separation between rings. In a similar manner, the stent can be made shorter by reducing the number of rings or decreasing the spacing between rings. Also variable spacing of the rings is envisioned for accomplishing a variety of purposes including increased hoop strength at a particular section of the stent. Also, it is envisioned that the two or more longitudinals could be utilized for this stent design with a maximum number being 32.

FIGS. 2 and 3 illustrate the joining of the longitudinals to the rings. Specifically the longitudinals can be placed into cutouts in the form of notches 5 located on the outside perimeter of the ring 2. The longitudinals can then be spot welded, adhesively bonded or joined by any variety of means to the rings 2. It is also envisioned that the longitudinals could be placed on the inside perimeter of the ring 2, or holes could be mechanically or laser drilled through the ring 2 for placement therethrough of the longitudinals.

Figure 4:
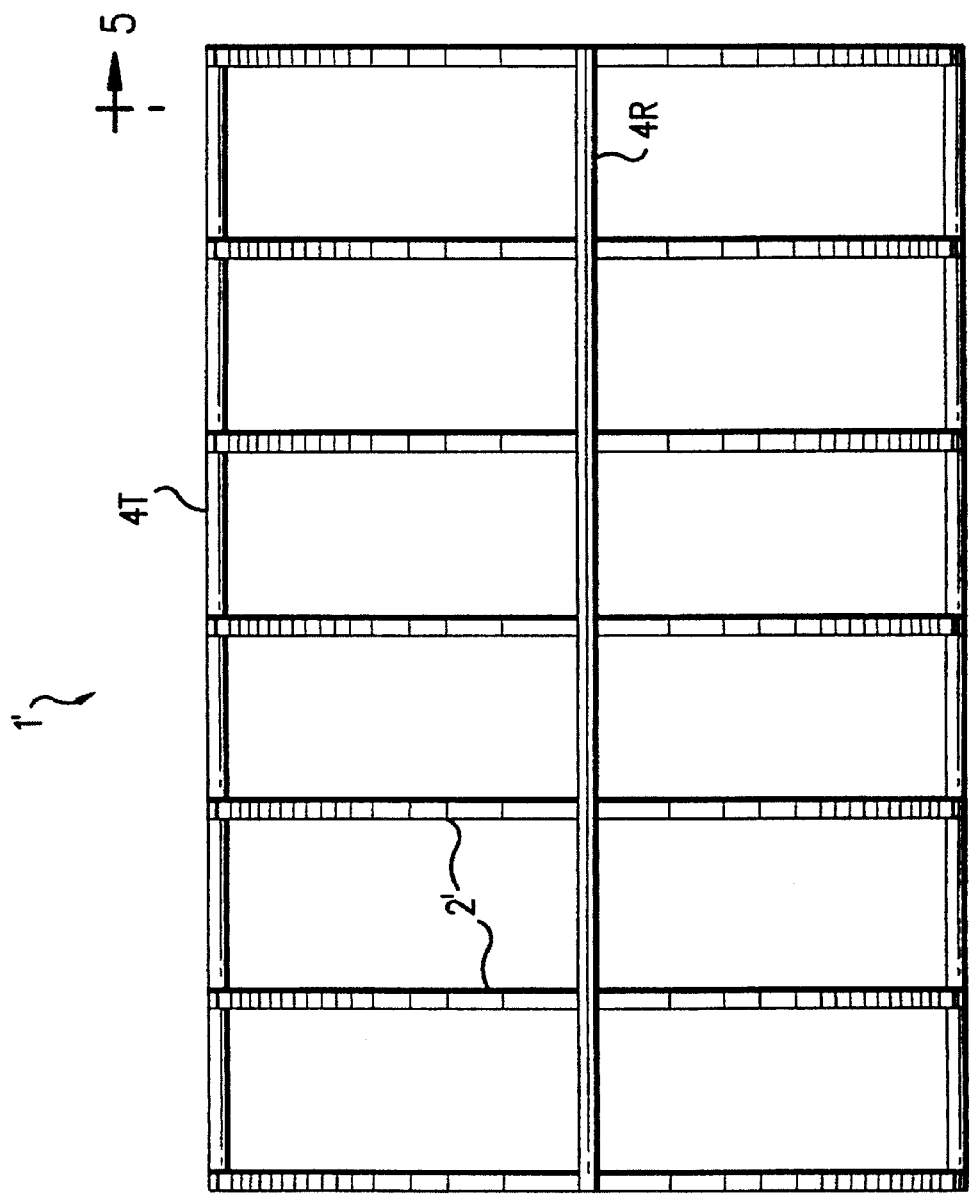
FIG. 4 is a side view of the stent prior to being mounted onto a stent delivery catheter; i.e., in the form of an initial structure.

FIGS. 4 and 5 illustrate a stent 1' shown in one particular form in which it could be fabricated; i.e., in an initial structure form. Specifically, FIGS. 4 and 5 show that this initial form of the stent 1' is a multiplicity of parallel ellipses or ovals 2' each oval having the same minor axis dimension m and major axis dimension M. The oval's minor axis passes through the center of the longitudinals 4L and 4R. The oval's major axis passes through the center of the longitudinals 4T and 4B. It is important to note that, if it is desired to have a final outside diameter D (as seen in FIG. 2) of the ring 2 after it is fully deployed, then it can be shown that D is given by the equation $D^2=\frac{1}{2}(m^2+M^2)$.

Figure 6:
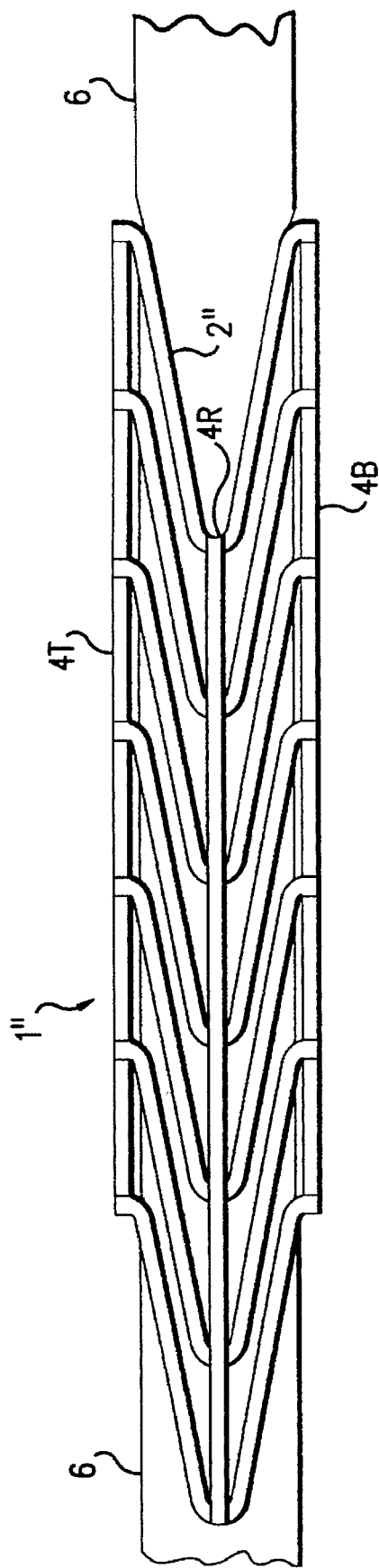
FIG. 6 is a side view of a pre-deployment form of the stent structure in which the ovals have been folded into a small diameter cylinder that is placed around a deflated balloon situated near the distal end of a stent delivery catheter.

To place the stent design of FIGS. 4 and 5 onto a balloon that is mounted near the distal end of a stent delivery catheter, it is necessary to fold the ovals 2' around that balloon. Specifically, the pre-deployment cylindrical stent 1" can be formed onto an expandable balloon 6 as shown in FIG. 6 by folding the ovals 2' about the dotted line F (which is the minor axis of the oval 2') as shown in FIG. 5. Specifically, as seen in FIG. 4, the top and bottom of the ovals 2' could be held stationery while the side longitudinals 4R and 4L are pushed to the left which results in the pre-deployment structure which is shown as the stent 1" in FIG. 6. An optimum design has the folded ovals 2" as shown in FIG. 6 with the stent 1" being a cylinder whose outside diameter is equal in size to the minor axis dimension m. When the balloon 6 of FIG. 6 is expanded, the pre-deployment stent 1" structure forms the post-deployment stent 1 structure having circular rings 2 as shown in FIGS. 1 and 2.

Figure 7:
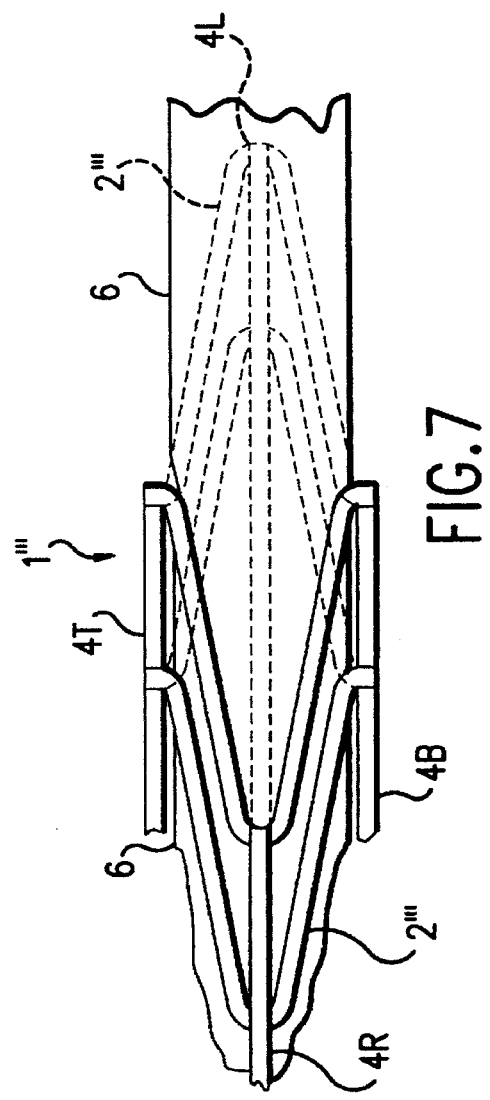
FIG. 7 is a partial side view of a pre-deployment stent structure showing only two of a multiplicity of folded ovals formed around an expandable balloon in which the ovals are folded in an alternative manner as compared with FIG. 6.

The stent 1''' is an alternative embodiment for a pre-deployment structure of the stent of the present invention as it is placed onto a balloon. Specifically, FIG. 7 shows 2 folded rings 2''' of a multiple ring stent 1'''. The stent 1''' being formed by holding the top and bottom of the stent 1' of FIG. 4 stationery while pushing the longitudinal 4R to the left and pushing the longitudinal 4L to the right. Like the stent 1" of FIG. 6, when mounted onto a balloon, the stent 1''' has a cylindrical shape with a diameter equal to the dimension m.

FIGS. 1 to 7 inclusive illustrate stents that employ longitudinals that are formed from generally straight wires. FIG. 8 shows an alternative embodiment of a stent 10 that has two undulating longitudinals. Specifically, the left side longitudinal 14L (shown as dotted lines) and the right side longitudinal 14R are each undulating shaped longitudinals. A stent such as stent 10 could have two or more undulating longitudinals. Such a stent would bend more easily during insertion into a vessel and would be more readily adaptable for placement in curved vessels such as some coronary arteries.

Typically, the rings and longitudinals of the stents would be made of the same material. Typical metals used for such a stent would be stainless steel, tantulum, titanium, or a shape memory metal such as Nitinol. If Nitinol is used, the stent would be heat treated into the shape at body temperature having circular rings 2 as shown in FIGS. 1 and 2. The rings could then be distorted into ovals as shown in FIGS. 4 and 5 and then mounted onto a stent delivery catheter which does not employ a balloon but is of the more general shape described in the previously cited U.S. Pat. No. 4,553, 545 by C. T. Dotter. Such a design would provide the desired stent structure having a multiplicity of generally circular rings instead of the Dotter design of a helical spring which inherently has a lesser hoop strength as compared to the present invention.

It should be understood that once the ovals are folded onto a stent delivery catheter, when they fully deploy, they do not form perfectly circular rings as shown in FIG. 2, but rather they are of a generally circular shape. Such comparatively small deviations from an exactly circular shape do not appreciably decrease hoop strength because they are in fact closed structures that are almost exactly circular.

It should also be understood that at least part of the end rings of the stent could be fabricated from or coated with a radiopaque metal such as tantalum or gold to provide a fluoroscopic indication of the stent position within a vessel. However, the other rings and the longitudinals could be made from a much less dense metal which would provide less obscuration of the central region within the stent. For example, the stent rings and longitudinals could all be fabricated from titanium or a titanium alloy except the end rings which could be formed from gold which is then plated with titanium. Thus, the entire outside surface of the stent would be titanium, which is known to be a comparatively non-thrombogenic metal while the gold in the end rings provides an improved fluoroscopic image of the stent extremities.

The dimensions of stent rings are typically 0.1 to 0.3 mm thick, with a width of 0.1 to 0.5 mm and an outside diameter D between 2.0 and 30.0 mm depending on the luminal diameter of the vessel into which it is inserted. The length of the stent could be between 1 and 10 cm. The wire diameter for the longitudinals would typically be between 0.05 and 0.5 min.

Although the designs of FIGS. 1 through 7 inclusive illustrate separate longitudinals attached to a multiplicity of rings, this invention also contemplates an initial stent structure which is chemically etched from thin-walled tubing having an oval transverse cross section. Thus the oval and longitudinals would be formed from a single piece of metal thus precluding the need for attaching the longitudinals to the rings. In a similar manner laser or EDM machining could be used to form the stent from a thin-walled tube.

It is further anticipated that a pre-deployment stent structure 20 as shown in FIG. 9 could be formed from a thin-walled cylindrical tube whose inside diameter is slightly smaller than the outside diameter of the balloon 6 shown in FIG. 6. A pattern such as that shown in either FIG. 6 or FIG. 7 could be photoetched onto a thin-walled metal cylinder. The one piece structure 20 shown in FIG. 9 has folded ovals 22 and longitudinals 23T, 24B, 24R and (not shown) 24L. This pre-deployment stent structure 20 could then be mounted onto the expandable balloon; the stent having sufficient elastic recoil to firmly grasp down onto the balloon.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A post-deployment stent structure for maintaining patency of a vessel of a human body comprising:

a multiplicity of closed and continuously formed, generally circular rings, the plane of each ring being generally parallel to the plane of each adjacent ring, the rings having a generally common longitudinal axis which is perpendicular to the plane of each ring, at least two of the rings being spaced apart from each other; and a multiplicity of structures forming longitudinals, at least one longitudinal being fixedly attached to at least two of the rings and at least one longitudinal being adapted to maintain an essentially unchanged shape in the absence of the multiplicity of generally circular rings and at least one of said longitudinals having an undulating shape for enhancing longitudinal flexibility of said post-deployment stent structure.

2. The stent of claim 1 wherein the longitudinals are generally elongated structures that lie generally parallel to the common longitudinal axis of the generally circular rings.

3. The stent of claim 1 wherein the rings are formed in unitary construction with the longitudinals from a single piece of metal.

4. The stent of claim 3 wherein the single piece of metal is generally in the form of a thin-walled cylinder.

5. The stent of claim 1 wherein the at least one longitudinal is spaced apart from all other longitudinals.

6. The stent of claim 1 wherein each longitudinal is spaced apart from every other longitudinal.

7. The stent of claim 1 wherein at least one of the longitudinals is a linearly directed, elongated structure.

8. The stent of claim 1 wherein all the longitudinals are of an undulating shape so as to enhance longitudinal flexibility.

9. The stent of claim 1 wherein the rings and longitudinals are made from titanium.

10. The stent of claim 1 wherein the multiplicity of circular rings has exactly two end rings which are those rings which have an adjacent ring on only one side and at least one interior ring which has adjacent rings on both sides, at least some portion of the end rings being formed from a metal having a higher density as compared to the density of the metal of the at least one interior ring.

11. The stent of claim 1 wherein the stent is formed from a metal having a shape memory characteristic.

12. An initial structure that is capable of being formed into a pre-deployment stent structure which in turn is capable of being deployed into a post-deployment stent structure for placement within a vessel of the human body, the initial structure comprising:

a multiplicity of flat ovals, the plane of each oval being generally parallel to the plane of all other ovals, the ovals having a common longitudinal axis which is perpendicular to the plane of each oval and which longitudinal axis passes through the geometric center of the ovals; and a multiplicity of longitudinals which are fixedly attached to the ovals, the longitudinals being positioned onto the ovals so as to be generally parallel to the longitudinal axis of the ovals, at least one of the longitudinals being spaced apart from all other longitudinals and having an undulating contour for enhancing longitudinal flexibility of said initial structure.

13. The initial structure of claim 12 wherein the ovals and the longitudinals are unitary.

14. A pre-deployment stent structure which is capable of being deployed into a post-deployment stent structure for placement within a vessel of the human body, the pre-deployment structure being formed from an initial structure which consists of a multiplicity of flat ovals, the plane of each oval of said initial structure being generally parallel to the plane of all other ovals, the ovals also having a minor axis and a major axis and a minor axis dimension and a major axis dimension; the ovals having a common longitudinal axis which is perpendicular to the plane of each oval and which longitudinal axis passes through the geometric center of the ovals; and a multiplicity of longitudinals at least one of which is fixedly attached to at least two of the ovals, the longitudinals being of unitary construction with the ovals from a single metallic structure, at least one of said longitudinals having an undulating contour for enhancing longitudinal flexibility of said pre-deployment stent structure.

15. The pre-deployment stent structure of claim 14 wherein one side of the ovals is folded in one direction and the opposite side of the ovals is folded in the opposite direction to form a pre-deployment structure of a generally cylindrical shape.

16. The pre-deployment stent structure of claim 14 wherein the outer diameter of the generally cylindrical pre-deployment stent structure is approximately the same as the minor axis dimension of the oval.

17. A post-deployment stent structure for maintaining patency of a vessel of a human body comprising:

a multiplicity of closed and continuously formed, generally circular rings, the plane of each ring being generally parallel to the plane of each adjacent ring, the rings having a generally common longitudinal axis which is perpendicular to the plane of each ring, at least two of the rings being spaced apart from each other; and a multiplicity of structures forming longitudinals, at least one longitudinal being fixedly attached to at least two of the rings, at least one longitudinal being spaced apart form all other longitudinals and at least one of said longitudinals having an undulating contour for enhancing longitudinal flexibility of said post-deployment stent.

18. a post-deployment stent structure for maintaining patency of a vessel of a human body comprising:

a multiplicity of closed and continuously formed, generally circular rings, the plane of each ring being generally parallel to the plane of each adjacent ring, the rings having a generally common longitudinal axis which is perpendicular to the plane of each ring, at least two of the rings being spaced apart from each other; and a multiplicity of structures forming longitudinals, at least one longitudinal being fixedly attached to at least two of the rings, at least one longitudinal being adapted to maintain an essentially unchanged shape in the absence of any externally applied force, and at least one of said longitudinals having an undulating contour for enhancing longitudinal flexibility of said post-deployment stent structure.

19. A post-deployment stent structure for maintaining patency of a vessel of a human body comprising:

a multiplicity of closed and continuously formed, generally circular rings, the plane of each ring being generally parallel to the plane of each adjacent ring, the rings having a generally common longitudinal axis which is perpendicular to the plane of each ring, at least two of the rings being spaced apart from each other; and a multiplicity of structures forming longitudinals, at least one longitudinal being fixedly attached to at least two of the rings, the longitudinals being of unitary construction with the generally circular rings from a single piece of thin-walled metal tubing and at least one of said longitudinals having an undulating contour for enhancing longitudinal flexibility of said post-deployment stent structure.

20. A post-deployment stent structure for maintaining patency of a vessel of a human body comprising:

a multiplicity of closed and continuously formed, generally circular rings, the plane of each ring being generally parallel to the plane of each adjacent ring, the rings having a generally common longitudinal axis which is perpendicular to the plane of each ring, at least two of the rings being spaced apart from each other; and a multiplicity of structures forming longitudinals, at least one longitudinal being fixedly attached to at least two of the rings and at least one longitudinal having an undulating shape so as to enhance the longitudinal flexibility of the post-deployment stent structure.

21. A predeployment stent structure adapted for placement in curved vessels of the coronary arteries, the stent structure being in the form of a thin-walled metal cylinder having a longitudinal axis, the stent including at least two undulating longitudinal structures each longitudinal structure having a multiplicity of straight sections and undulating sections with each straight section being joined continuously to at least one undulating section, the straight sections of all of the longitudinal structures being generally parallel to the longitudinal axis of the stent, the undulating sections of each longitudinal structure being of a generally curved shape so as to allow each undulating longitudinal structure to readily expand and contract in length when the stent is bent while passing through a curved coronary artery.

22. The deployment stent structure of claim 21 wherein each undulating section is in the general form of a sine wave.

23. A post-deployment stent structure for maintaining patency of a vessel of a human body comprising:

a multiplicity of closed and continuously formed generally circular rings, the plane of each ring being generally parallel to the plane of each adjacent ring, the rings having a generally common longitudinal axis which is perpendicular to the plane of each ring, at least two of said rings being spaced apart from each other and having a pair of opposing end rings positioned on opposing sides of at least one interior ring, at least a portion of at least one of said end rings being formed from a metal having a higher density as compared to the density of the metal of said at least one interior ring; and, a multiplicity of structures forming longitudinals, at least one longitudinal being fixedly attached to at least two of the rings and at least one longitudinal being adapted to maintain an essentially unchanged shape in the absence of the multiplicity of generally circular rings.

* * * * *

UNITED STATES PATENT AND TRADEMARK OFFICE
CERTIFICATE OF CORRECTION

PATENT NO.    : 5,643,312
DATED         : July 1, 1997
INVENTOR(S)   : Robert E. Fischell et al.

It is certified that error appears in the above-identified patent and that said Letters Patent is hereby corrected as shown below:

Column 4,
Line 47, insert the following sentence;
-- Another method to form the pre-deployment stent is by etching the correct pattern onto a thin, flat metal plate, then forming a tube from that plate and then making a longitudinal weld to form a cylindrically shaped structure which is, in fact, the pre-deployment stent structure 20 shown in Fig. 9. --

Signed and Sealed this

Twenty-fourth Day of December, 2002

JAMES E. ROGAN
*Director of the United States Patent and Trademark Office*